United States Patent [19]

Tokunaga

[11] Patent Number: 4,739,102
[45] Date of Patent: Apr. 19, 1988

[54] INDIVIDUAL BETA-FORM CRYSTALS OF TERAKIS-(3-(3,5-DI-T-BUTYL-4-HYDROXY-PHENYL)-PROPIONYLOXYMETHYL)-METHANE AND PROCESS FOR ITS MANUFACTURE

[75] Inventor: Mitsukuni Tokunaga, Tokyo, Japan

[73] Assignee: Ciba-Geigy Corporation, Ardsley, N.Y.

[21] Appl. No.: 43,900

[22] Filed: Apr. 29, 1987

[30] Foreign Application Priority Data

Apr. 30, 1986 [JP]  Japan ................................. 61-99925

[51] Int. Cl.$^4$ ............................................. C07C 69/76
[52] U.S. Cl. ........................................................ 560/75
[58] Field of Search ................................. 560/75, 61

[56] References Cited

U.S. PATENT DOCUMENTS

| | | | |
|---|---|---|---|
| 3,644,482 | 2/1972 | Dexter et al. | 560/75 |
| 3,657,322 | 4/1972 | Dexter et al. | 560/75 |
| 4,405,807 | 9/1983 | Hasui et al. | 560/75 |

FOREIGN PATENT DOCUMENTS

| | | | |
|---|---|---|---|
| 1177092 | 10/1984 | Canada | 560/75 |
| 32459 | 7/1981 | European Pat. Off. | 560/61 |
| 210131 | 1/1987 | European Pat. Off. | |
| 54376 | 3/1967 | Fed. Rep. of Germany | 560/75 |
| 56-12341 | 2/1981 | Japan . | |
| 6012342 | 2/1981 | Japan | 560/61 |
| 9222445 | 12/1984 | Japan | 560/75 |
| 1081789 | 8/1967 | United Kingdom . | |
| 1187317 | 4/1970 | United Kingdom . | |

OTHER PUBLICATIONS

C.A. 101, 191363g (1984).

*Primary Examiner*—Paul J. Killos
*Attorney, Agent, or Firm*—Luther A. R. Hall

[57] ABSTRACT

A new crystal form of tetrakis-[3-(3,5-di-t-butyl-4-hydroxyphenyl)propionyloxymethyl]-methane is disclosed. It is an individual $\beta$-modification crystal form in substantially parallelepipedal to cubic shape. A method of preparation of this new crystal form is likewise disclosed.

7 Claims, 2 Drawing Sheets

INDIVIDUAL BETA-FORM CRYSTALS OF TERAKIS-(3-(3,5-DI-T-BUTYL-4-HYDROXY-PHENYL)-PROPIONYLOXYMETHYL)-METHANE AND PROCESS FOR ITS MANUFACTURE

The present invention relates to tetrakis-[3-(3,5-di-t-butyl-4-hydroxyphenyl)-propionyloxymethyl]-methane [hereinafter called compound (1)] in a new crystal form, comprising individual β-modification crystals in substantially parallelepipedal to cubic shape, and a process for the production thereof.

Compound (1) is disclosed e.g. in U.S. Pat. No. 3,657,322 and has been accepted as an excellent anti-deterioration agent against heat, oxidation and light for organic material such as synthetic polymers like polyolefines, polyesters, polystyrenes, polyvinyl chlorides, polyurethanes, polyacetals etc., animal and vegetable oils, hydrocarbon oils, fatty acid esters, lubricants, etc. The stabilising agent comprising compound (1) available on the market is, however, aggregate of fine crystals, namely in granular form or fine powder form, resulting in low bulk density, inferior fluidity and easily scattering. Such powder leads to poor productivity and causes environmental problems. The latter are particularly critical. Various studies therefore have been made to overcome these problems.

Compound (1) has been known, as disclosed in U.S. Pat. No. 4,405,807 to have 4 crystal forms, i.e. α-form, β-form, γ-form and δ-form. A further form, i.e. the λ-form, is described in published European Patent Application No. 210 131. The various crystal forms are identified by X-ray diffraction, melting points and IR absorption spectrum. U.S. Pat. No. 4,405,807 also discloses δ-form crystals of compound (1) and a manufacturing process thereof, respectively. Compound (1) disclosed is, however, in the form of an aggregate of small crystals, thus readily breakable at handling.

According to U.S. Pat. No. 4,405,807, the δ-form crystals are prepared by the transesterification reaction of low-alkyl 3-(3,5-di-t-butyl-4-hydroxyphenyl)propionate [hereinafter called compound (2)] with pentaerythritol, in the presence of compound (3) expressed by the formula

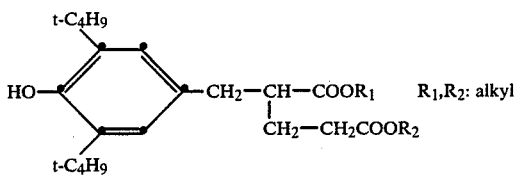

An alcohol capable of forming a molecular adduct with the product of the above transesterification reaction [compound (1)] is subsequently added to form a molecular adduct, followed by the recrystallization from methanol and/or ethanol. This process is not economical, as it indispensably requires the presence of compound (3) and the isolation of the molecular adduct is necessary, which results in an increased number of steps.

Japanese Patent Kokai Sho discloses spherical or semispherical γ-form crystals of compound (1). The said crystals, however, melt at a temperature so low as to tend to cause fusion and agglomeration during storage and transportation. In the preparation of said crystal structure, molten compound (1) is dropped on a flat and solid surface, wherein isolated and purified compound (1) is used as the starting material. Therefore, this process requires additional procedures to the conventional one and is likely to deteriorate compound (1), the starting material, by melting it.

The purpose of the present invention is to provide new crystals of known compound (1), a well known anti-deterioration agent for organic material. The new crystal form found has improved fluidity and bulk density and mechanical strength high enough not to be crushed during handling, storage and/or transportation. Thus they are stable in quality and cause no dust problem. Another purpose is to provide with a manufacturing process thereof.

The invention is, therefore, for tetrakis-[3-(3,5-di-t-butyl -4-hydroxyphenyl)-propionyloxymethyl]-methane in a new crystal form, comprising individual β-modification crystals in substantially parallelepipedal to cubic shape. Preferably, the crystal particles having a particle diameter <0.1 mm share no more than 15% by weight. The particularly preferred particle size distribution is the following:

>1 mm ≦5%
0.1–1 mm ≧80%
<0.1 mm ≦15%

The crystal of compound (1) of the present invention having a new state inherits the melting point from the conventional marketed product of compound (1), as both are β-modification crystals. On the other hand, since the crystal of the present invention is single and individual and not an aggregate, its mechanical strength is remarkably improved. Thus, the crystal of the present invention does not cause dust problems. As mentioned above, the conventional β-form crystals are an aggregate, which tends to be readily crushed and reform agglomerates. The single crystals of the present invention are substantially parallelepipedal to cubic. Since the crystals of the present invention have an improved mechanical strength, they can be used to prepare a commercial product while keeping their original size, instead of pulverizing like conventional β-crystals. The product, e.g. as stabilising agent, possesses high bulk density and high fluidity, i.e. good processability.

The present invention further relates to a process for the production of tetrakis-[3-(3,5-di-t-butyl-4-hydroxyphenyl)-propionyloxymethyl]-methane [hereinafter called compound (1)] in a new crystal form of individual β-modification with substantial parallelepipedal to cubic shape, characterized by crystallizing compound (1) from a crystallization solvent selected from ethanol, methanol or a mixture thereof, in the presence of a mixture A comprising 10–90% of methyl(or ethyl)-3-(3,5-di-t-butyl-4-hydroxyphenyl)propionate and 90–10% of hydroxymethyl-tris-[3-(3,5-di-t-butyl-4-hydroxyphenyl)propionyloxymethyl]-methane in a weight ratio of 0.05–0.66 to compound (1) wherein the solvent is used in a weight ratio of 0.25–2.0 to the total weight of the mixture A and compound (1), and in the presence of water in a weight ratio of 0.02 to 0.1 to the solvent.

Hydroxymethyltris-[3-(3,5-di-t-butyl-4-hydroxyphenyl)-propionyloxymethyl]-methane, hereinafter called compound (4) is of the formula

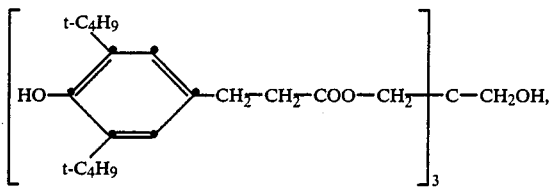

methyl(or ethyl)-3-(3,5-di-t-butyl-4-hydroxyphenyl)-propionate is hereinafter called compound (2).

When the solution containing the above mentioned compounds is stirred while cooling, compound (1) in individual β-modification form with almost cubic shape is obtained.

The compound (1) used in the process according to this invention is preferably prepared by the transesterification of pentaerythritol and compound (2) which is preferably the methyl ester. The method for esterification is as described in for example U.S. Pat. No. 3,657,322. An example of the concrete process will be given in the below mentioned example. Compound (2) is generally used in excess to pentaerythritol in the said transesterification reaction. In the reaction mixture after the completion of the reaction, there exists as impurities mainly non-reacted starting material compound (2) and compound (4) in addition to compound (1). The compound (4) is tri-ester substituted compound formed by the reaction between three hydroxyl groups out of four hydroxyl groups of pentaerythritol and compound (4). The ratio of compound (2) to compound (4) varies from 1:9–9:1 depending on the excess ratio of the compound (2) filled in the reaction vessel and the progress of the reaction. In the present invention, however, it is necessary that the weight ratio of the mixture A comprising the above two compounds resides within the range of 0.05–0.66, preferably 0.1–0.5, based on the weight of compound (1). Although there exist impurities other than compounds (2) and (4), their amount is so low under the reaction condition which provides practical yield that the presence of such impurities is not bothersome at all in the process of the present invention.

When the reaction is proceeded under a good condition, the ratio of the mixture A to compound (I) may fall below the range mentioned above. In such a case, it is necessary to add mixture A to suffice the above mentioned range by any measure such as adding a part of the mixture A removed from the previous crystallization step to the reaction mixture of the following reaction, etc. Although the ratio of the mixture A can be increased by intentionally keeping the reactivity low or increasing the excess ratio of compound (2), such methods are economically disadvantageous. It is the simplest way of the methods for recovering the mixture A from the crystallization process to use a part of a mother liquor, which contains the mixture A, as a part of the crystallization solvent for the following run. It is, however, also possible to use the residue collected after the distillation of the solvent from the mother liquor in the following crystallization solution.

When the ratio of the mixture A is lower than the above mentioned range, the crystals obtained are of α-form or β-form in fine powder or granular shape. When the ratio of the mixture A is above the present invention, the crystals obtained are of fine powder and simultaneously the deposition of crystal is not sufficient, namely resulting in drastically low crystallization yield.

The solvents must be methanol or/and ethanol which contains the above mentioned amount of water. When the amount of water exceeds the given range, the crystal obtained becomes fine powder or granule. When the amount of the solvent exceeds the given range, the crystal obtained also becomes fine powder or granule. A preferred weight ratio of water to the solvent is from 0.03 to 0.05.

The mixture having the above mentioned components becomes a homogeneous solution at the boiling point of the solvent used or the temperature below the said point. Crystals start precipitation by gradually lowering the temperature by cooling, preferably after the solution obtained has been clarified by filtration. In order to smoothly progress the precipitation of the crystals and growth, β-crystals of compound (1) may be added as seed. It is preferred to add the seed at 50°–60° C., generally.

When the stirring becomes difficult by the progress of the precipitation of the crystals, a solvent may be added to dilute the crystal slurry. Moreover, a small amount of water can be added to increase the deposition rate. In this occasion, if it is after the deposition of the most part of crystals, the presence of the solvent and water exceeding the limit of the invention by such addition is allowable. The crystal slurry is desirably cooled to a temperature no higher than about 20° C. and filtered to obtain the crystals of compound (1) in order to assure a better yield.

The transesterification reaction per se is carried out without any or in the presence of a solvent. Di-polar solvents, particularly dimethylsulfoxide and dimethylformamide are preferred solvents. Other usable solvents are tetrahydrofuran, dioxane, pyridine, dimethylacetamide, nitrobenzene, 1,2-dimethoxyethane, o-nitroanisole, acetonitrile, propionitrile, t-butylalcohol, etc. The reaction advantageously proceeds in the presence of a catalyst, preferably, lower alkoxides of alkali metals such as lithium methoxide or sodium methoxide. Other usable catalysts are e.g. alkali metal or alkaline earth metal hydrides, such as sodium hydride, lithium hydride or calcium hydride, or metallic sodium or potassium. When a catalyst is used in the transesterification, the reaction mixture must be neutralized with an acid prior to the addition of a crystallization solvent. For neutralization of the reaction catalyst, commonly used carboxylic acid such as acetic acids and organic sulfonic acids are employed.

The apparatus used to the crystallization according to the present invention can be anything so long as it can keep the solution and the crystal slurry under mild stirring. It is another advantage of the present invention that the crystallization does not require any specific apparatus but can be performed in the most ordinary stirring vessel.

Although it is preferred to carry out the crystallization step directly with the product obtained from the transesterification process [preparation of compound (1)], it is also possible to start from a compound (1) otherwise obtained. The crystals of compound (1) can be dissolved in the methanol or/and ethanol and the required amounts of mixture A and water can be added. The crystallization step is then carried out as described above.

The present invention relates further to the product which can be obtained according to the process of this invention described hereinbefore.

The shape of the crystal of compound (1) formed according to the process of this invention is a larger individual and substantially cubic or parallelepipedal, preferably cubic particle as shown by the microphotograph of FIG. 2. The crystals hardly contain fine particles. Since the x-ray difraction (Cu-Kα) pattern of the present crystal shows the characteristic peaks of the β-crystal of compound (1) as disclosed in the above mentioned U.S. Pat. No. 4,405,807, i.e. difraction angle θ has 5 peaks within the range of 5°–10.5°, the crystals can be decided to have β-crystal form.

The individual particle of β-crystal of compound (1) and its manufacturing process have not been known. By the present invention, the said particle was confirmed for the first time and its production became possible. Since the present crystal is β-form, it has the melting point as high as 114° C., which causes less agglomeration. As shown in the below mentioned examples, the crystal of the present invention has higher bulk density and better fluidity compared to the conventional granular or finely powdery compound (1). In handling of the crystals of the present invention, scattering of fine powder is hardly recognized. Since the crystal is individual particle but not aggregate, it can be washed easily after filtration and a highly pure product can be easily obtained. The crystal is difficultly breakably during drying, transportation, etc., procedures. It is another characteristic of the present crystal that it keeps excellent fluidity and high bulk density even after being broken in a certain degree. Since compound (1) exerts its anti-oxidation effect by being dispersed and dissolved in a substrate, its activity as anti-oxidant does not depend on the crystal form or particle size. However, the said characteristics of the crystal form of the present invention of compound (1) increase the commercial value of the compound of the present invention.

The individual β-form crystals of compound (1) in substantially parallelepipedal to cubic shape of the present invention can be used in the same manner as commercially available compound (1) as stabilising agent for organic material susceptible to degradation under ordinary conditions. Such organic material may be synthetic organic material disclosed in the literature previously mentioned. The stabilising agent of the present invention may be added to the organic material in an amount of 0.005–5% by weight based on the organic material composition. A particularly preferred amount for polyolefines is about 0.05–2% by weight, most preferably about 0.1–1%.

As in the case of conventional compound (1), the stabilising agent of the present invention can be jointly used with other stabilizers and/or additives. For instance, anti-oxidants, anti-ozonants, heat-stabilizers, UV-absorbers, coloring material, dyestuffs, pigments, metal-chelating agents are jointly usable.

The present invention is further explained by the following examples.

EXAMPLE 1

231.5 g of methyl 3-(3,5-di-t-butyl-4-hydroxyphenyl) propionate and 24.5 g of pentaerythritol are mixed and heated to 100° C. in a 4-necked flask (500 ml) equipped with a stirrer, a reflux condenser, a thermometer and a nitrogen gas inlet. To the mixture are added 0.2 g of lithium amide and 8 g of tetraline while stirring. The mixture is then heated at 130°–140° C./39 mbar for 1 hour. Then, the temperature is risen to 150°–160° C./6,5–13 mbar and kept at the same temperature for 5 hours to complete the reaction, while distilling off a small amount of methanol generated and tetraline.

The reaction mixture is cooled to 110° C. and the pressure is adjusted to atmospheric by introducing nitrogen gas. The reaction mixture is neutralized by adding 1.0 g of glacial acetic acid. The reaction mixture obtained contains the above-mentioned mixture A, i.e. compounds (2) (i.e. the methyl ester) and (4), in the weight ratio of about 0.2 to compound (1). 160 g of methanol (weight ratio of 0.8 to the total weight of compound (1) and the mixture A) and 5 g of water (weight ratio of 0.03 to methanol) are added carefully at about 100° C. After the addition, the mixture is heated to 65°–70° C. to make it a homogeneous solution. Insoluble material is filtered off while hot.

Then, a small amount of cubic β-modification crystals of compound (1) is added at about 60° C. by gradually lowering the temperature. When the temperature is lowered to 35° C. by cooling with air, the solution is a thick slurry. It is diluted by adding portion-wise 80 ml of methanol (water content: 3% by weight). The slurry is cooled to 20° C. and crystals deposited are collected by filtration and washed with cold methanol and dried.

The crystals obtained show a particle size distribution as follows

>1 mm 2,1%
0,5–1 mm 16,4%
0,2–0,5 mm 36,6%
0,1–0,2 mm 33,6%
<0,1 mm 11,3%

150 g of compound (1) in the new cubic crystal form are obtained. Yield of crystallization: 90%. The crystals so obtained have substantially cubic or parallelepipedal shape as shown in FIG. 2. X-ray difraction pattern (Cu-Kα) is given in FIG. 3. The crystals are confirmed as β-form from 5 sharp peaks of difraction angle 2θ in 5°–10.5° C. It melts at 114.3° C., which also supports that the crystals are β-form. The bulk density is 0.53, angle of slide 39° C. and falling velocity 18 sec/100 ml. These data show that the crystals have more preferred properties than conventional commercial products.

EXAMPLE 2

Example 1 is repeated except that ethanol is used instead of methanol.

Comparative example 1 is a sample of compound (1) in conventional fine powdery crystal α-form. Melting point: 123.6° C.

Comparative example 2. In the process of example 1, water is added in an amount of 1.6 g (0.01 based on methanol). Fine powdery α-crystals are obtained. Melting point: 120.3° C.

For comparison, properties of the products obtained by example 1, example 2, comparative examples 1 and 2 and commercially available compound (1) (powdery β-form, Comparison 3) are shown in Table 1.

TABLE 1

| physical properties | samples taken from | | | | |
| --- | --- | --- | --- | --- | --- |
| | Example 1 | Example 2 | Comparison 1 | Comparison 2 | Comparison 3 |
| mp (°C.)[1] | 114.3 | 114.3 | 123.6 | 120.3 | 114.4 |
| Bulk Density[2] | 0.53 | 0.54 | 0.25 | 0.35 | 0.37 |
| Angle of Slide (°) | 39 | 40 | 45 | 44 | 51 |
| Falling Velocity (sec/100 ml) | 18 | 18 | 60 | 45 | 200 |
| Crystal | β | β | α | α | β |

TABLE 1-continued

| physical properties | samples taken from | | | | |
|---|---|---|---|---|---|
| | Example 1 | Example 2 | Comparison 1 | Comparison 2 | Comparison 3 |
| modification Crystal shape | Cubic | Cubic | Powder | Powder | Powder |

[1]measured by FP 5-type melting point measure of Mettler Co.
[2]measured by Powder Tester of Hosokawa micron K.K.

EXAMPLE 3-20

Solutions of various composition as shown in Table 2 are prepared from the reaction mixture synthesized by the manner shown in Example 1 and compounds (1), (2) and (4) prepared separately. The solutions are then subjected to crystallization. Individual and almost cubic form of β-crystals of compound (I) are obtained in all cases. Table 2 shows melting points and crystallization yield of the crystals obtained.

TABLE 2

| Example | Weight ratio of | | | Melting point | Yield (%) |
|---|---|---|---|---|---|
| | Mixture A/ Compound (1) | Solvent/ Compound (1) + Mixture A | Water/ Solvent | | |
| 3 | 0.25 | 0.97* | 0.03 | 113.9 | 82 |
| 4 | 0.33 | 0.25* | 0.03 | 114.3 | 80 |
| 5 | 0.25 | 0.33* | 0.02 | 114.8 | 78.5 |
| 6 | 0.20 | 0.65* | 0.02 | 114.3 | 84.5 |
| 7 | 0.20 | 0.65** | 0.03 | 114.3 | 82 |
| 8 | 0.20 | 0.64* | 0.04 | 113.9 | 88 |
| 9 | 0.20 | 0.64* | 0.05 | 113.9 | 90 |
| 10 | 0.20 | 0.60* | 0.10 | 114.4 | 91.5 |
| 11 | 0.10 | 0.79* | 0.03 | 114.8 | 90 |
| 12 | 0.50 | 0.65* | 0.02 | 113.8 | 60 |
| 13 | 0.50 | 0.65* | 0.03 | 113.9 | 68 |
| 14 | 0.50 | 0.64* | 0.04 | 113.5 | 69 |
| 15 | 0.50 | 0.63* | 0.05 | 114.1 | 73 |
| 16 | 0.33 | 1.47* | 0.02 | 114.8 | 79 |
| 17 | 0.33 | 1.46* | 0.03 | 114.8 | 74 |
| 18 | 0.33 | 1.44* | 0.04 | 114.8 | 84 |
| 19 | 0.33 | 1.43* | 0.05 | 113.9 | 86 |
| 20 | 0.40 | 1.80* | 0.03 | 114.0 | 85 |

*Solvent: methanol
**Solvent: ethanol

EXAMPLE 21

Bulk densities, angles of slide and falling velocities are measured with samples obtained by some representative examples.

The results are shown in Table 3.

TABLE 3

| Example | Bulk density | Angles of slide (°) | Falling Velocity (sec/100 ml) |
|---|---|---|---|
| 3 | 0.53 | 40 | 20 |
| 6 | 0.54 | 40 | 21 |
| 7 | 0.49 | 42 | 22 |
| 9 | 0.46 | 40 | 25 |
| 11 | 0.53 | 40 | 21 |
| 12 | 0.51 | 46 | 24 |
| 18 | 0.51 | 44 | 25 |
| 19 | 0.51 | 41 | 25 |

EXAMPLE 22

The mechanical strength of the compound of Example 1 is tested by means of the turbula agitation test. 100 g of the substance are agitated in a flask for 7 hours at room temperature by turbula. The high mechanical strength of the crystals is demonstrated by the fact that the particle size distribution remains approximately unchanged after the above-mentioned treatment as shown in Table 4.

TABLE 4

| Particle size distribution before turbula | | Particle size distribution after 7h turbula | |
|---|---|---|---|
| >1 mm | 2,1% | >1 mm | 1,1% |
| 0,5-1 mm | 16,4% | 0,5-1 mm | 21,6% |
| 0,2-0,5 mm | 36,6% | 0,2-0,5 mm | 35,2% |
| 0,1-0,2 mm | 33,6% | 0,1-0,2 mm | 29,4% |
| <0,1 mm | 11,3% | <0,1 mm | 12,7% |

Figure 1:
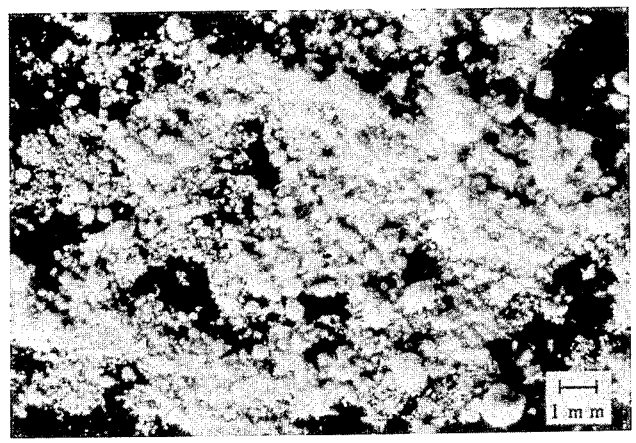
FIG. 1 is a microphotograph of conventionally available compound (1) (powdery β-form).
Figure 2:
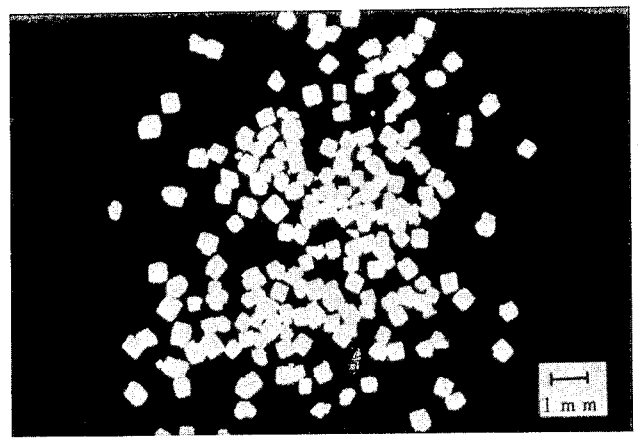
FIG. 2 shows a microphotograph of compound (1) obtained by the process of the present invention.
Figure 3:
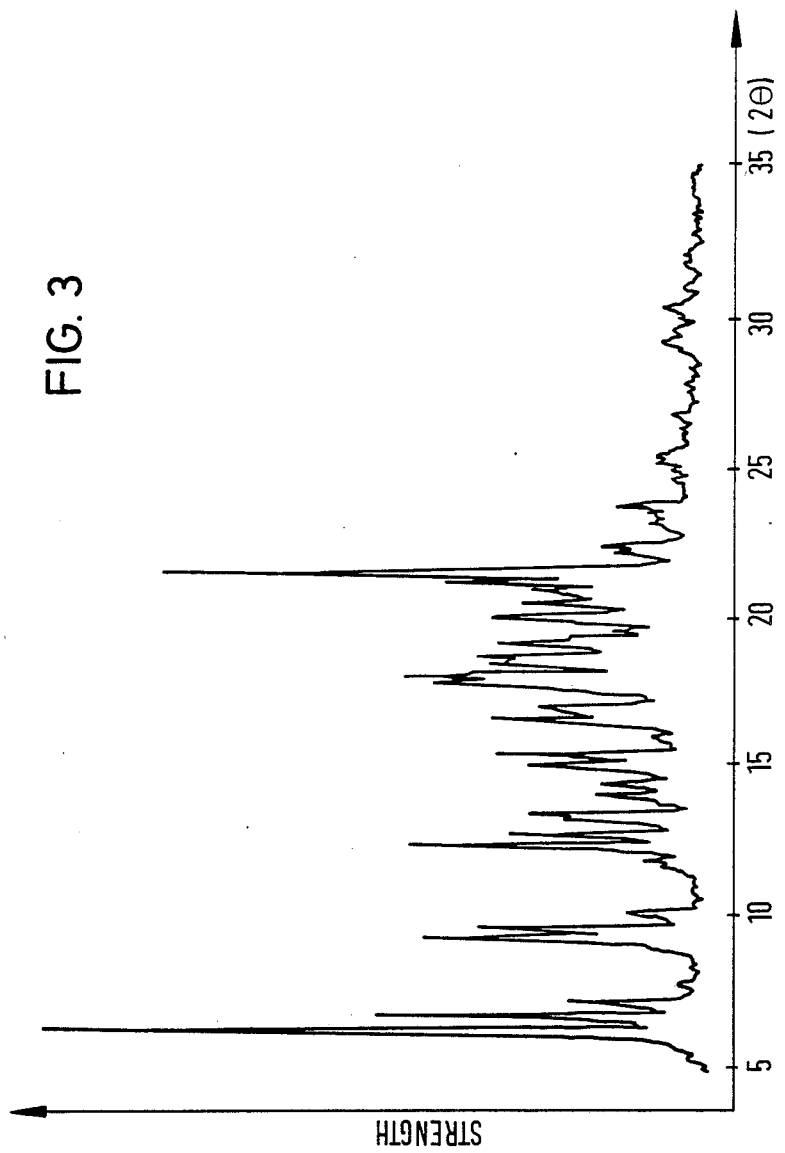
FIG. 3 shows an X-ray difraction pattern of compound (1) obtained by the process of the present invention.

What is claimed is:

1. Tetrakis-[3-(3,5-di-t-butyl-4-hydroxyphenyl)-propionyloxymethyl]methane in a new crystal form, comprising individual β-modification crystals in substantially parallelepipedal to cubic shape.

2. The compound of claim 1, wherein the crystal particles having a particle diameter <0.1 mm share no more than 15% by weight.

3. The compound of claim 1 wherein the crystal particle size distribution is as follows:
>1 mm ≦ 5%
0.1-1 mm ≧ 80%
<0.1 mm ≦ 15%

4. A process for the production of tetrakis-[3-(3,5-di-t-butyl -4-hydroxyphenyl)-propionyloxymethyl]-methane [hereinafter called compound (1)] in a new crystal form of individual β-modification with substantial parallelepipedal to cubic shape, characterized by crystallizing compound (1) from a crystallization solvent selected from ethanol, methanol or a mixture thereof, in the presence of a mixture A comprising 10-90% of methyl(or ethyl)-3-(3,5-di-t-butyl-4-hydroxyphenyl)propionate and 90 - 10% of hydroxymethyl-tris-[3-(3,5-di-t-butyl-4-hydroxyphenyl)-propionyloxymethyl]-methane in a weight ratio of 0.05-0.66 to compound (1) wherein the solvent is used in a weight ratio of 0.25-2.0 to the total weight of the mixture A and compound (1), and in the presence of water in a weight ratio of 0.02 to 0.1 to the solvent.

5. The process of claim 4, wherein the weight ratio of the mixture A to compound (1) is from 0.1 to 0.5.

6. The process of claim 4, wherein the weight ratio of water to the solvent is from 0.03 to 0.05.

7. Tetrakis-[3-(3,5-di-t-butyl-4-hydroxyphenyl)-propionyloxymethyl]methane obtainable according to the process described in claim 4.

* * * * *